US008968659B2

(12) United States Patent
Davies et al.

(10) Patent No.: US 8,968,659 B2
(45) Date of Patent: Mar. 3, 2015

(54) SAMPLE DISPENSING

(75) Inventors: Mark Davies, Limerick (IE); Tara Dalton, Limerick (IE)

(73) Assignee: Stokes Bio Limited, Carlsbad, CA (US)

(*) Notice: Subject to any disclaimer, the term of this patent is extended or adjusted under 35 U.S.C. 154(b) by 690 days.

(21) Appl. No.: 12/683,882

(22) Filed: Jan. 7, 2010

(65) Prior Publication Data
US 2010/0120635 A1    May 13, 2010

Related U.S. Application Data

(63) Continuation-in-part of application No. 12/617,286, filed on Nov. 12, 2009, which is a continuation of application No. 11/366,524, filed on Mar. 3, 2006, now Pat. No. 7,622,076, which is a continuation of application No. PCT/IE2004/000115, filed on Sep. 6, 2004.

(60) Provisional application No. 60/500,344, filed on Sep. 5, 2003, provisional application No. 60/500,345, filed on Sep. 5, 2003.

(51) Int. Cl.
G01N 1/18      (2006.01)
G01N 1/00      (2006.01)
G01N 33/00     (2006.01)
C40B 60/14     (2006.01)
B01F 5/00      (2006.01)
B01F 13/00     (2006.01)
B01L 3/00      (2006.01)
B01L 7/00      (2006.01)
G01N 35/08     (2006.01)
G01N 35/10     (2006.01)
G01N 35/00     (2006.01)

(52) U.S. Cl.
CPC .......... B01F 5/0057 (2013.01); B01F 13/0059 (2013.01); B01F 13/0071 (2013.01); B01L 3/50273 (2013.01); B01L 7/525 (2013.01); G01N 35/08 (2013.01); B01L 2200/0636 (2013.01); B01L 2200/0673 (2013.01); B01L 2300/0816 (2013.01); B01L 2300/0861 (2013.01); B01L 2300/087 (2013.01); B01L 2300/185 (2013.01); B01L 2400/0409 (2013.01); B01L 2400/0487 (2013.01); G01N 35/1095 (2013.01); G01N 2035/00514 (2013.01)
USPC .......................................... 422/68.1; 422/50

(58) Field of Classification Search
CPC .......... G01N 1/18; G01N 1/00; G01N 33/00; G01N 1/10; G01N 1/02
USPC ............ 422/57, 50, 68.1, 500; 506/26, 40, 33
See application file for complete search history.

(56) References Cited

U.S. PATENT DOCUMENTS

| 4,766,082 | A | * | 8/1988 | Marteau D'Autry ......... 436/178 |
|---|---|---|---|---|
| 5,102,517 | A | | 4/1992 | Fuchs et al. |
| 5,270,183 | A | | 12/1993 | Corbett et al. |
| 6,193,471 | B1 | | 2/2001 | Paul |
| 6,355,164 | B1 | * | 3/2002 | Wendell et al. ............ 210/198.2 |
| 6,557,427 | B2 | | 5/2003 | Weigl et al. |
| 6,907,895 | B2 | | 6/2005 | Johnson et al. |
| 7,077,152 | B2 | | 7/2006 | Karp |
| 7,129,091 | B2 | | 10/2006 | Ismagilov et al. |
| 7,189,580 | B2 | | 3/2007 | Beebe et al. |
| 7,235,405 | B2 | | 6/2007 | Charles et al. |
| 7,238,268 | B2 | | 7/2007 | Ramsey et al. |
| 7,294,503 | B2 | | 11/2007 | Quake et al. |
| 7,622,076 | B2 | | 11/2009 | Davies et al. |
| 2002/0060156 | A1 | | 5/2002 | Mathies et al. |
| 2004/0211659 | A1 | | 10/2004 | Velev |
| 2005/0048581 | A1 | | 3/2005 | Chiu et al. |
| 2005/0202489 | A1 | | 9/2005 | Cho et al. |
| 2005/0272159 | A1 | | 12/2005 | Ismagilov et al. |
| 2007/0117212 | A1 | * | 5/2007 | Kautz et al. ................ 436/137 |
| 2007/0134209 | A1 | | 6/2007 | Oakey |
| 2010/0022414 | A1 | | 1/2010 | Link et al. |
| 2010/0041086 | A1 | | 2/2010 | Pamula et al. |
| 2010/0059120 | A1 | | 3/2010 | Tian |
| 2010/0092987 | A1 | | 4/2010 | Davies et al. |
| 2010/0297685 | A1 | | 11/2010 | Davies et al. |

FOREIGN PATENT DOCUMENTS

| WO | WO03/016558 A1 * | 2/2003 | ............... C12Q 1/68 |
|---|---|---|---|
| WO | WO2004/038363 | 6/2004 | |
| WO | 2005/002730 | 1/2005 | |
| WO | 2005/023427 | 3/2005 | |
| WO | WO2005023427 | 3/2005 | |
| WO | 2005/059512 | 6/2005 | |
| WO | 2007/091228 | 8/2007 | |
| WO | WO2007091228 | 8/2007 | |
| WO | WO2007091229 | 8/2007 | |
| WO | WO2007091230 | 8/2007 | |
| WO | WO2008038259 | 4/2008 | |

OTHER PUBLICATIONS

"Fluoromed" [online] retrieved from http://fluoromed.com/products/perfluoroperhydrophenanthrene.html., May 17, 2011.
Bernard, et al., "Real-time PCR technology for cancer diagnostics.", *Clinical Chemistry* 48(8), 1178-85 (2002).

(Continued)

*Primary Examiner* — Christine T Mui

(57) ABSTRACT

The present invention generally relates to systems and methods for mixing and dispensing a sample droplet from a microfluidic system, such as a liquid bridge system. In certain embodiments, the invention provides systems for mixing and dispensing sample droplets, including a sample acquisition stage, a device for mixing sample droplets to form sample droplets wrapped in an immiscible carrier fluid, a dispensing port, and at least one channel connecting the stage, the droplet mixing device, and the port, in which the system is configured to establish a siphoning effect for dispensing the droplets.

18 Claims, 2 Drawing Sheets

(56) References Cited

OTHER PUBLICATIONS

Chung, G., et al., "Human neural stem cell growth and differentiation in a gradient-generating microfluidic device", *Lab on a Chip*, 5, 401-406 (2005).

Curran, K., et al., "Liquid bridge instability applied to microfluidics", *Microfluid Nanofluid* 1, 336-345 (2005).

Edgar, M., et al., "Selective Encapsulation of Single Cells and Subcellular Organelles into Picoliter- and Femtoliter-Volume Droplets", *Anal. Chem.* 77, 1539-1544 (2005).

Nakano, M., et al., "Single-Molecule PCR using water-in-oil emulsion", *Journal of Biotechnology* 102, 117-124 (2003).

Newport, D., et al., "Microfluidics for Genetic Cancer Diagnostics", *La Houille Blanche* 1, 26-33 (Jan.-Feb. 2006).

Thouas, G.A., et al., "The 'GO' system-a novel method of microculture for in vitro development of mouse zygotes to the blastocyst stage", *Reproduction* 126, 161-169 (2003).

Brouzes, Eric et al., "Droplet Microfluidic Technology for Single-Cell High-throughput Screening", *Proceedings of the National Academy of Sciences*, vol. 106, No. 34, 2009, 14195-14200.

Kumaresan, P. et al., "High-Throughput Single Copy DNA Amplification and Cel Analysis in Engineered Nanoliter Droplets", *Analytical Chemistry*, vol. 80, 2008, 3522-3529.

Medkova, Martina et al., "Analyzing Cancer at Single Cell Resolution with Droplet Technology", *American Association of Cancer Research*, RainDance Technologies, Apr. 19, 2010.

Nakano, H. et al., "High Speed Polymerase Chain Reaction in Constant Flow", *Biosci. Biotech. Biochem*, vol. 58 (2), Jun. 12, 2014, 349-352.

\* cited by examiner

SAMPLE DISPENSING

RELATED APPLICATIONS

The present application is a continuation-in-part of U.S. patent application Ser. No. 12/617,286, filed Nov. 12, 2009, which is a continuation of U.S. patent application Ser. No. 11/366,524, filed Mar. 3, 2006, which is a continuation of PCT/IE2004/000115 filed Sep. 6, 2004 and published in English, claiming the priorities of U.S. patent application Ser. Nos. 60/500,344 and 60/500,345, both filed on Sep. 5, 2003. The contents of each of these applications are incorporated by reference herein in their entirety.

FIELD OF THE INVENTION

The present invention generally relates to systems and methods for dispensing a sample droplet from a microfluidic system, such as a liquid bridge system.

BACKGROUND

Microfluidics involves micro-scale devices that handle small volumes of fluids. Because microfluidics can accurately and reproducibly control small fluid volumes, in particular volumes less than 1 µl, it provides significant cost-savings. The use of microfluidics technology reduces cycle times, shortens time-to-results, and increase throughput. Furthermore incorporation of microfluidics technology enhances system integration and automation.

An exemplary microfluidic device involves liquid bridge technology. Liquid bridges allow sample droplet formation or mixing utilizing immiscible fluids. In a liquid bridge, a sample droplet at an end of an inlet port enters a chamber that is filled with a carrier fluid. The carrier fluid is immiscible with the sample droplet. The sample droplet expands until it is large enough to span a gap between inlet and outlet ports. Droplet mixing can be accomplished in many ways, for example, by adjusting flow rate or by introducing a second sample droplet to the first sample droplet, forming an unstable funicular bridge that subsequently ruptures from the inlet port. After rupturing from the inlet port, the mixed sample droplet enters the outlet port, surrounded by the carrier fluid from the chamber. At that point in time, the droplet may be analyzed or undergo further manipulation, for example PCR amplification, QPCR, or immunoassay.

SUMMARY

Of particular usefulness is collection of individual intact mixed sample droplets from a liquid bridge system after the droplets have been analyzed or have undergone further manipulation. Such a sample dispensing system involves acquiring samples from a first vessel at atmospheric pressure, processes the samples, and then dispensing the samples to a second vessel also at atmospheric pressure A typical liquid bridge system operates below atmospheric pressure due to viscous friction of the carrier fluid. Thus application of a force is required to overcome a pressure differential that exists between the system and a vessel at atmospheric pressure in order to dispense sample droplets to the vessel, i.e., there is a need to raise the pressure back to atmospheric at the dispensing port. Typically, a pump is used to drive flow in a liquid bridge system, which is suitable for many applications using a liquid bridge system, such as those described in Davies et al. (International patent publication numbers WO 2007/091230, WO 2008/038259, WO 2007/091230, WO 2007/091228, and WO 2005/023427), the contents of each of which are incorporated by reference herein in their entirety.

However, pumps are not optimal to dispense intact mixed sample droplets from a liquid bridge system. In order to use a pump to overcome a pressure differential that exists between the system and a vessel at atmospheric pressure, mixed sample droplets at sub-atmospheric pressure in the system would need to be flowed through the pump to be dispensed to the vessel. Pumps are generally driven by rotary vanes, and these vanes would slice through sample droplets formed in a liquid bridge system; rupturing the droplets and preventing contents of the droplets from being collected. Additionally, rupture of the droplets would disperse contents of the droplets throughout the liquid bridge system, resulting in contamination of the system. There is a need for systems and methods for dispensing intact sample droplets from microfluidic systems, such as liquid bridge systems.

The present invention generally relates to systems and methods for dispensing intact sample droplets from microfluidic systems, such as a liquid bridge systems. According to the invention, sample dispensing is accomplished by configuring systems of the invention to generate a siphoning effect, i.e., flow that is driven by difference in hydrostatic pressure without any need for pumping. The siphoning effect drives flow through the system and generates a force necessary to overcome a pressure differential that exists between sample droplets in the liquid bridge system and a vessel at atmospheric pressure, allowing for individual intact sample droplets to be dispensed to vessels at atmospheric pressure. Because the siphoning effect is generated without use of pumps, sample droplets are not ruptured and intact droplets are dispensed to a vessel so that contents of the droplets, e.g., PCR products, may be collected for subsequent manipulation and further analysis.

Systems of the invention may include may different components and may include numerous configurations, as long as the configuration of the system generates a siphoning effect. For example, systems of the invention may include a sample acquisition stage, a device for mixing sample droplets to form mixed sample droplets wrapped in an immiscible carrier fluid, a dispensing port, and at least one channel connecting the stage, the droplet mixing device, and the port, in which the system is configured to establish a siphoning effect for dispensing the droplets. An exemplary droplet mixing device is a liquid bridge.

Systems of the invention may also include a priming pump for initially priming the system with a carrier fluid that is immiscible with the sample. Once sample acquisition begins, the priming pump is turned off so as not to rupture the sample droplets that are being dispensed. Systems of the invention may also include a thermocycler. Systems of the invention may also include at least one valve to control flow through the system.

Sample droplets may be dispensed to any type of vessel, such as a container or a well plate (e.g., 96 well or 384 well). In certain embodiments, individual sample droplets are dispensed into separate wells of a well plate. In other embodiments, systems of the invention dispense the sample droplets as discrete spots on a surface to form an array of droplets. In certain embodiments, the systems of the invention dispense wrapped droplets.

Systems of the invention produce droplets that are wrapped in an immiscible carrier fluid. For dispensing purposes, it is advantageous to ensure that a substantial portion of the carrier fluid is not dispensed into a collecting vessel. In certain embodiments, flow rate is used to ensure that a substantial portion of the carrier fluid is not dispensed into the collecting vessel. The flow is controlled such that the dispensing port can be moved over a waste container to collect the carrier fluid and then moved over the collecting vessel to dispense the sample droplets. In this manner, a substantial a portion of the carrier fluid is not dispensed into the collecting vessel.

In other embodiments, a pump is positioned after the droplet forming device and off-line of the channel through which the droplets flow. The pump removes the carrier fluid surrounding the droplet prior to the droplet being dispensed. In this manner, a substantial a portion of the carrier fluid is not dispensed into the collecting vessel.

Sample droplets may include any type of molecule, e.g., nucleic acids (e.g., DNA or RNA), proteins, small organic molecules, small inorganic molecules, or synthetic molecules. In particular embodiments, the droplet includes nucleic acids.

Another aspect of the invention provides a method for mixing and dispensing sample droplets, including establishing a siphoning effect; acquiring a sample; mixing sample droplets to form mixed sample droplets wrapped in an immiscible carrier fluid; and using the siphoning effect to dispense the sample droplets. Methods of the invention may further include amplifying contents of the sample droplets.

DETAILED DESCRIPTION

The present invention generally relates to systems and methods for dispensing sample droplets from microfluidic systems, such as a liquid bridge systems. According to the invention, sample dispensing is accomplished by configuring systems of the invention to generate a siphoning effect. The siphoning effect refers to flow that is driven by a difference in hydrostatic pressure without any need for pumping. The effect is produced by configuring a system such that a dispensing end or port is lower than a fluid surface at an acquisition point, e.g., a sample acquisition stage. The system may include any number of additional components that are positioned at an intermediate point in the system. Those intermediate components may be higher or lower than the acquisition point as long as the dispensing end is lower than the fluid surface at the acquisition point.

Figure 1:
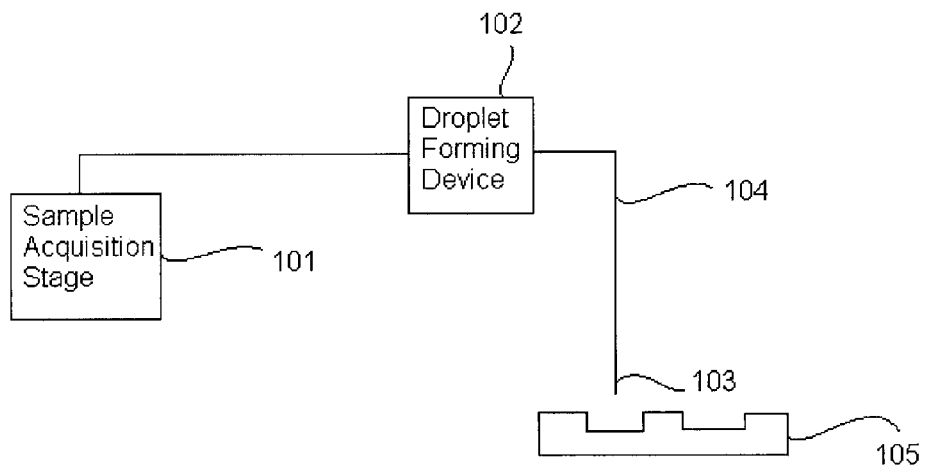
FIG. 1 is a schematic showing an exemplary configuration of one embodiment of systems of the invention.

Numerous systems configured to produce a siphoning effect for sample dispensing are provided herein. FIG. 1 shows an exemplary configuration of a system 100 of the invention. This configuration includes a sample acquisition stage 101, a device for mixing sample droplets to form mixed sample droplets wrapped in an immiscible carrier fluid 102, a dispensing port 103; and at least one channel 104 connecting the stage 101, the droplet mixing device 102, and the port 103. The system 100 is configured to establish a siphoning effect for dispensing the droplets into vessel 105 by positioning the dispensing port 103 below a level of the sample acquisition stage 101. The droplet mixing device 102 may be positioned higher or lower than the sample acquisition stage 101.

Sample droplets flow through the channel 104 due to head difference between an inlet of the channel 104 and an outlet of the channel 104, allowing the droplets to flow toward a lower potential energy state. Once started, the siphoning effect requires no additional energy to keep the fluid flowing from the acquisition stage 101 to the dispensing port 103, i.e., no pumps are required. The siphoning effect will pull the sample droplets through the channel 104 until the level falls below the sample acquisition stage 101, allowing for the sample to be dispensed into a vessel 105 at a point below the sample acquisition stage 101. Energy is conserved because the dispensing port 103 is lower than the fluid level at the sample acquisition stage 101. Flow rates through the system and height differential between the sample acquisition stage 101 and the dispensing port 103 can be determined using Bernoulli's equation. Application of Bernoulli's equation to siphons is well known in the art. See e.g., Edwards et al. (Introduction to Fluid Mechanics, Oxford University Press, 102007); Chadwick et al. (Hydraulics in Civil and Environmental Engineering, 103rd edition, SPON, 101998); and Douglas et al. (Fluid Mechanics, 105th edition, Prentiss Hall, 102006), the contents of each of which are incorporated by reference herein in their entirety.

Varying the height between the sample acquisition stage 101 and the sample dispensing port 103 changes the flow rate of the system 100. In certain embodiments, the height difference between sample acquisition stage 101 and the sample dispensing port 103 remains constant. In alternative embodiments, the height difference between the sample acquisition stage 101 and the sample dispensing port 103 varies during operation of the system. For example, the height difference between the sample acquisition stage 101 and the sample dispensing port 103 varies depending on whether a sample is being acquired or a sample is being dispensed.

Systems of the invention may further include a pump to prime the system and also provide the initial energy required to initiate the siphoning effect. Any pump known in the art may be used with systems of the invention because once sample acquisition begins, the priming pump is turned off so as not to rupture the sample droplets that are being dispensed. An exemplary pump is shown in Davies et al. (WO 2007/091229, incorporated by reference herein in its entirety). Other commercially available pumps can also be used.

Sample droplets are formed at the acquisition stage 101. Any device may be used at the acquisition stage 101 that results in forming of sample droplets that are wrapped in an immiscible carrier fluid. Determination of the immiscible fluid to be used is based on the properties of the channel and of the sample. If the sample is a hydrophilic sample, the fluid used should be a hydrophobic fluid. An exemplary hydrophobic fluid is oil, such as AS5 silicone oil (commercially available from Union Carbide Corporation, Danbury, Conn.). Alternatively, if the sample is a hydrophobic sample, the fluid to used should be a hydrophilic fluid. One of skill in the art will readily be able to determine the type of fluid to be used based on the properties of the sample.

The wrapped droplets may be formed, for example, by dipping an open ended tube into a vessel. Exemplary sample acquisition devices are shown in McGuire et al. (U.S. patent application Ser. No. 12/468,367). Alternatively, droplets may be formed by flowing a continuous plug of sample to a liquid bridge and using the liquid bridge to form the droplets.

After droplet formation, sample droplets are mixed by droplet mixing device 102. Droplet mixing device 102 may be any device that is capable of mixing sample droplets to form mixed sample droplets wrapped in an immiscible carrier fluid. An exemplary droplet mixing device is a liquid bridge.

Liquid bridges allow sample droplet mixing utilizing immiscible fluids. In a liquid bridge, a sample droplet at an end of an inlet port enters a chamber that is filled with a carrier fluid. The carrier fluid is immiscible with the sample droplet. The sample droplet expands until it is large enough to span a gap between inlet and outlet ports. Droplet mixing can be accomplished in many ways, for example, by adjusting flow rate or by introducing a second sample droplet to the first sample droplet, forming an unstable funicular bridge that subsequently ruptures from the inlet port. After rupturing from the inlet port, the mixed sample droplet enters the outlet port, surrounded by the carrier fluid from the chamber. An exemplary liquid bridge system is shown in Davies et al. (International patent publication number WO 2007/091228), the contents of which are incorporated by reference herein in their entirety.

After droplet mixing in the droplet mixing device 102, the samples droplets flow through channel 104 to dispensing port 103. In certain embodiments, the end of channel 104 acts as dispensing port 103. In other embodiments, channel 104, connects to dispensing port 103 that is a distinct and separate component from channel 104.

Droplet dispensing may be accomplished in numerous ways. In certain embodiments, it is advantageous to ensure that a substantial portion of the carrier fluid is not dispensed into a collecting vessel. In one manner, flow rate is used to ensure that a substantial portion of the carrier fluid is not dispensed into the collecting vessel. The flow is controlled such that the dispensing port can be moved over a waste container to dispense the carrier fluid surrounding the droplets, and then moved over a collecting vessel to dispense the sample droplets. In this manner, a substantial a portion of the carrier fluid is not dispensed into the collecting vessel. Movement of the dispensing port is controlled by at least one robotics system.

In another manner, a pump is positioned after the droplet forming device and off-line of the channel 104 through which the droplets flow. The pump removes the carrier fluid surrounding the droplet prior to the droplet being dispensed. In this manner, a substantial portion of the carrier fluid is not dispensed into the collecting vessel.

In other embodiments, droplets are dispensed wrapped in the immiscible carrier fluid, i.e., a collecting vessel contains a static wrapped droplet. Dispensing wrapped droplets is desirable for storage purposes because the droplets will be protected by the carrier fluid and will not evaporate. Also, dispensing of wrapped droplets allows for re-sampling and re-using the same sample droplet.

Figure 3:
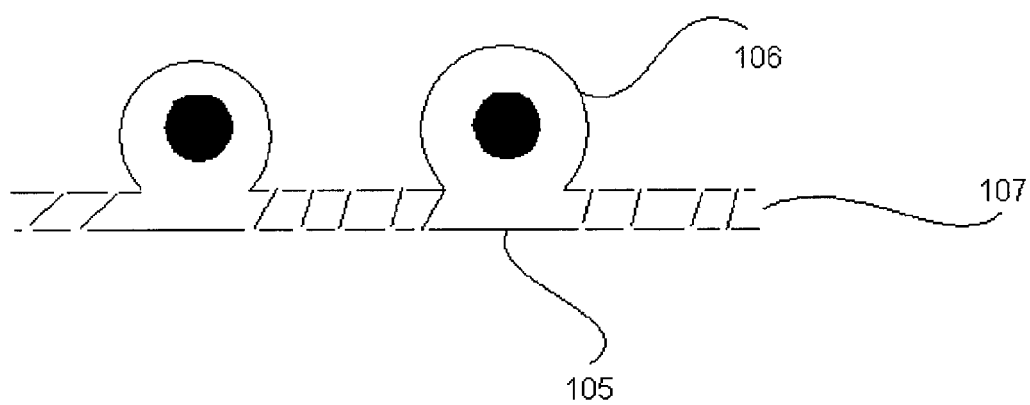
FIG. 3 is a schematic showing dispensing of wrapped droplets to a vessel in which there is continuous flow from a dispensing port.

In these embodiments, the carrier fluid is not removed from around the sample droplet and the dispensing port 104 simply dispenses the wrapped droplet to the collecting vessel. Flow may be controlled so that dispensing is continuous or discontinuous. With continuous flow, a wrapped droplet 106 is dispensed from dispensing port 104 to vessel 105. See FIG. 3. After the droplet is dispensed, the dispensing port 104 moves to another location for dispensing of another droplet to vessel 105. While moving, the dispensing port continues to dispense carrier fluid, thus laying down a thin film 107 of carrier fluid across the vessel. Wrapped droplets may be dispensed to form an ordered array of wrapped droplets.

Figure 4:
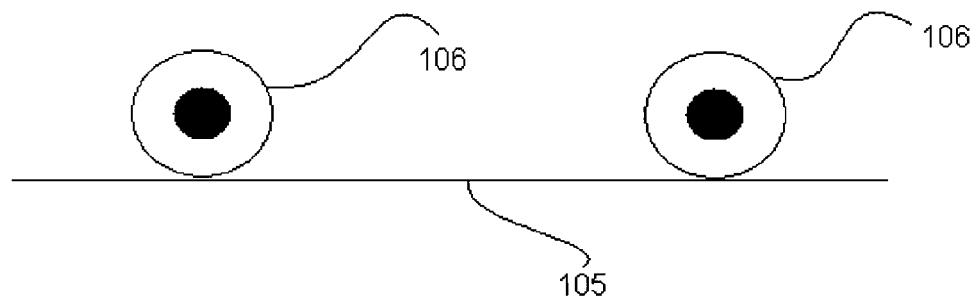
FIG. 4 is a schematic showing dispensing of wrapped droplets to a vessel in which there is discontinuous flow from a dispensing port.

With discontinuous flow, a wrapped droplet 106 is dispensed from dispensing port 104 to vessel 105. See FIG. 4. After the droplet is dispensed, the dispensing port 104 moves to another location for dispensing another droplet to vessel 105. While the dispensing port is moving, no carrier fluid is dispensed from the port 104, thus resulting in production of an array of discrete droplets. Wrapped droplets may be dispensed to form an ordered array of wrapped droplets.

In other embodiments, the collecting vessel includes a layer of fluid that is immiscible with the sample droplet, such that droplets are dispensed into the layer of fluid. In certain embodiments, the layer of fluid and the carrier fluid surrounding the droplet are the same. In alternative embodiments, the layer of fluid and the carrier fluid surrounding the droplet are different. In these embodiment, carrier fluid surrounding the droplet may be removed prior to dispensing. Alternatively, the carrier fluid need not be removed, and the wrapped droplets may be dispensed into the layer of fluid on the collecting vessel.

In other embodiments, the collecting vessel includes an aqueous solution, for example a well plate having buffer in each well of the plate. In this embodiment, carrier fluid surrounding the droplet may be removed prior to dispensing. Alternatively, the carrier fluid need not be removed, and the wrapped droplets may be dispensed into the aqueous solution.

The droplets are dispensed from the dispensing port 103 to a vessel 105. Exemplary vessels include plates (e.g., 96 well or 384 well plates), eppendorf tubes, vials, beakers, flasks, centrifuge tubes, capillary tubes, cryogenic vials, bags, cups, or containers. The vessel can be made of any material suitable to interact with biological or chemical species. Exemplary materials include TEFLON (commercially available from Dupont, Wilmington, Del.), polytetrafluoroethylene (PTFE; commercially available from Dupont, Wilmington, Del.), polymethyl methacrylate (PMMA; commercially available from TexLoc, Fort Worth, Tex.), polyurethane (commercially available from TexLoc, Fort Worth, Tex.), polycarbonate (commercially available from TexLoc, Fort Worth, Tex.), polystyrene (commercially available from TexLoc, Fort Worth, Tex.), polyetheretherketone (PEEK; commercially available from TexLoc, Fort Worth, Tex.), perfluoroalkoxy (PFA; commercially available from TexLoc, Fort Worth, Tex.), or Fluorinated ethylene propylene (FEP; commercially available from TexLoc, Fort Worth, Tex.).

In certain embodiments, individual sample droplets are dispensed into separate wells of a well plate. In other embodiments, systems of the invention dispense the sample droplets as discrete spots on a surface to form an array of droplets.

Sample droplets may include any type of molecule or molecules, e.g., nucleic acids (e.g., DNA or RNA), proteins, small organic molecules, small inorganic molecules, antibodies, or aptamers. In particular embodiments, the droplet includes nucleic acids.

Figure 2:
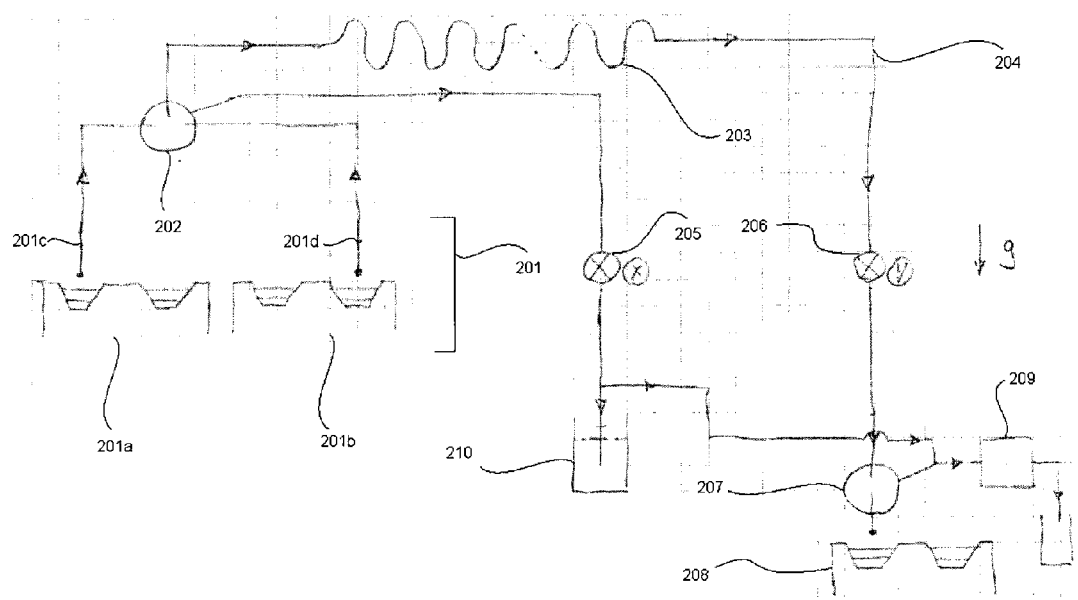
FIG. 2 is a schematic showing another exemplary configuration of another embodiment of systems of the invention.

FIG. 2 is a schematic showing another embodiment of system 200 of the invention. This embodiment of the system may be used for amplifying nucleic acids, e.g., PCR or QPCR. In this embodiment, sample acquisition stage 201 includes two well plates (201a and 201b). Plate 201a includes nucleic acids to be amplified, while plate 201b includes reagents for amplifying the nucleic acids. A typical PCR or QPCR reaction contains: fluorescent double-stranded binding dye, Taq polymerase, deoxynucleotides of type A, C, G, and T, magnesium chloride, forward and reverse primers and subject cDNA, all suspended within an aqueous buffer. Reactants, however, may be assigned into two broad groups: universal and reaction specific. Universal reactants are those common to every amplification reaction, and include: fluorescent double-stranded binding dye, Taq polymerase, deoxynucleotides A, C, G and T, and magnesium chloride. Reaction specific reactants include the forward and reverse primers and sample nucleic acid.

The samples are acquired using sample acquisition devices 201c and 201d, and individual sample droplets are formed at this point. Exemplary sample acquisition devices are shown in McGuire et al. (U.S. patent application Ser. No. 12/468,367). Once acquired, the individual sample droplets are mixed at droplet mixing device 202. Droplet mixing device 202 may be any device that is capable of mixing sample droplets to produce a mixed droplet wrapped in an immiscible carrier fluid. An exemplary droplet mixing device is a liquid bridge system. An exemplary liquid bridge system is shown in Davies et al. (International patent publication number WO 2007/091228). After droplet mixing, the droplets flow to thermocycler 203 where the nucleic acids in the droplets are amplified. An exemplary thermocycler and methods of fluidly connecting a thermocycler to a liquid bridge system are shown in Davies et al. (International patent publication numbers WO 2005/023427, WO 2007/091230, and WO 2008/038259, each of which is incorporated by reference herein in its entirety). The thermocycler can be connected to an optical detecting device to detect the products of the PCR reaction. An optical detecting device and methods for connecting the device to the thermocycler are shown in Davies et al. (International patent publication numbers WO 2007/091230 and WO 2008/038259, each of which is incorporated by reference herein in its entirety).

After amplification, the samples are flowed to dispensing port 207. In this embodiment, flow rate is used to ensure that a substantial portion of the carrier fluid is not dispensed into the collecting vessel. The flow is controlled such that the dispensing port can be moved over a waste container to collect the carrier fluid and then moved over the collecting vessel to dispense the sample droplets. In this manner, a substantial portion of the carrier fluid is not dispensed into the collecting vessel. Movement of the dispensing port is controlled by at least one robotics system.

The sample droplets are dispensed into wells of vessel 208. In certain embodiments, multiple droplets may be dispensed into a single well. Alternatively, the system can dispense a single droplet into each well.

System 200 of the invention includes a pump 209 to prime the system and also provide the initial energy required to initiate the siphoning effect. Any pump known in the art may be used with systems of the invention because once sample acquisition begins, the priming pump is turned off so as not to rupture the formed sample droplets that are being dispensed. An exemplary pump is shown in Davies et al. (WO 2007/091229). Other commercially available pumps can also be used.

The components of system 200 are connected by channel 204. Droplets flow from sample acquisition stage 201 through channel 204 to dispensing port 207. The system 200 is configured to establish a siphoning effect for dispensing the droplets into vessel 208 by positioning the dispensing port 207 below a level of the sample acquisition stage 201. The droplet carrier device 202 and thermocycler 203 may be positioned higher or lower than the sample acquisition stage 201. System 200 is also shown with valves 205 and 206. These valves can be opened and closed as desired to assist in controlling flow of the system.

Incorporation by Reference and Equivalents

References and citations to other documents, such as patents, patent applications, patent publications, journals, books, papers, web contents, have been made throughout this disclosure. All such documents are hereby incorporated herein by reference in their entirety for all purposes. Various modifications of the invention and many further embodiments thereof, in addition to those shown and described herein, will become apparent to those skilled in the art from the full contents of this document, including the references to the scientific and patent literature cited herein.

EXAMPLES

Example 1

Determining Height of Siphon

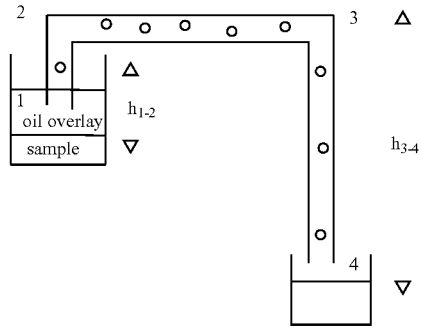

The schematic above shows a siphoning system designed to deliver a biphasic flow including sample droplets from a first vessel at atmospheric pressure to a second vessel at atmospheric pressure. Height difference between an inlet of a channel (shown near number 1) and an outlet of the channel (shown near number 4) drives flow through the system. Droplets are formed by alternating dipping into a sample at the inlet of the channel and back into an oil overlay (which is an example of a carrier fluid that is immiscible with the sample) such that no air enters the system. At a dispensing end, the sample is separated from the carrier fluid by a density difference between the two fluids.

A pressure drop is generated within the system, which is due to viscous friction in a laminar flow. Height differential between an acquisition stage and a dispensing port to obtain a desired siphoning effect for the system may be determined using Bernoulli's equation with a variable added to describe the viscous loss. The dynamic head is small in comparison to the pressure drop, and thus may be ignored in the equation, as shown in the calculation below. The pressure head due to the height difference therefore equals the viscous pressure loss to a very good approximation.

For biphasic flow, the pressure loss is generally greater, and therefore a larger height difference is required to drive the same flow. This increase in pressure loss is generally found by measurement, and it depends both on droplet size and droplet spacing in a given diameter channel.

Equation 1 below may be used to calculate the height differential between the acquisition stage and the dispensing port in order to obtain the desired siphoning effect.

$$p_1 + \tfrac{1}{2}\rho u_1^2 + \rho g h_1 = p_4 + \tfrac{1}{2}\rho u_4^2 + \rho g h_4 + p_2 \qquad \text{Equation 1}$$

Numbers 1 and 4 represent the immersion depth of the channel in a fluid. Number 1 shows that the channel is positioned just below the fluid level at the acquisition stage. Because the channel is approximately at the fluid level, $p_1 = p_{ab}$. Similarly, number 4 is positioned above the fluid level at the dispensing port, thus $p_4 = p_{ab}$. According $p_1 = p_4 = p_{ab}$. Because number 1 is positioned just outside of the channel, $u_1 = 0$.

Entering those values into Equation 1, the equation reduces to Equation 2 below.

$$pg(h_1-h_4)=\tfrac{1}{2}p(u_4^2)+p_2 \qquad \text{Equation 2}$$

$p_2$ is the pressure drop in the channel. The greater $p_2$, the less $p_4$.

$p_L=R_q$, where R is resistance: $R=8\ \mu L/\pi r^4$; or $R=128\ \mu L/\pi D^4$. D and L will vary depending on the system design. At present, small D values are used in the acquisition system and larger values in the thermal cycler. Because of the $D^4$ relationship, the pressure drops in the long lines are relatively small. For an order of magnitude calculation: L=0.2 m; D=0.17 mm. Thus: $R=128\times(5\times10^{-3})\times0.2/\pi(0.17\times10^{-3})^4=5\times10^{13}$.

A typical flow rate is $q=10\ \mu L/\min=10\times10^{-6}\times10^{-3}/60=1.67\times10^{-10}\ m^3/s$. $\Delta p_L=(5\times10^{13})\times(1.67\times10^{10})=8{,}350\ N/m^2$.

$u_4=q/A_x$ wherein $A_x=\pi D^2/4=\pi(0.17\times10^{-3})^2/4=2.27\times10^{-8}$. Thus $u_4=1.67\times10^{-10}/2.27\times10^{-8}=7.3\ mm/s$.

The dynamic head is equal to $\tfrac{1}{2}p(u_4^2)=\tfrac{1}{2}(10^3)(7.3\times10^{-3})^2=0.027\ N/m^2$. Because the value of the dynamic head is nominal, the dynamic head is therefore ignored in comparison to $p_L$ in Equation 2.

Inserting the above values into Equation 2, the equation reduces to $h_1-h_2=p_L/pg=8{,}350/10^4=0.8\ m$. Thus, the height of the siphon is approximately 0.8 m.

What is claimed is:

1. A system for mixing and dispensing sample droplets, the system comprising:
   at least one sample acquisition stage;
   a device for mixing sample droplets to produce a mixed sample droplet wrapped in an immiscible fluid;
   a variable height dispensing port;
   at least one channel fluidly communicating the stage, the droplet mixing device, and the port, and
   a vessel for collecting the sample droplet dispensed from the port, the vessel configured to contain a carrier fluid for receiving and protecting the sample droplet;
   wherein the dispensing port is positioned below the level of the sample acquisition stage, and wherein the system is configured to establish a siphoning effect for dispensing the droplets.

2. The system according to claim 1, wherein the droplet mixing device is a liquid bridge.

3. The system according to claim 1, further comprising a priming pump.

4. The system according to claim 1, further comprising a thermocycler.

5. The system according to claim 1, further comprising at least one valve to control flow through the system.

6. The system according to claim 1, wherein the sample droplets are dispensed into separate wells of a well plate.

7. The system according to claim 1, wherein the system dispenses the sample droplets as discrete spots on a surface to form an array of droplets.

8. The system according to claim 1, wherein the dispensing port dispenses the sample droplet to a first vessel, moves over a second vessel to dispense the carrier fluid, and then moves back over the first vessel to dispense another sample droplet.

9. The system according to claim 1, wherein the droplet comprises nucleic acids.

10. The system according to claim 1, wherein height between the sample acquisition stage and the dispensing port varies during sample acquisition and sample dispensing.

11. The system according to claim 1, wherein the system dispenses wrapped droplets.

12. A system for generating sample droplets comprising:
    at least one sample acquisition stage;
    a droplet generator, in fluid communication with the stage, for producing a sample droplet wrapped in an immiscible fluid;
    a dispensing port in fluid communication with the droplet generator for dispensing the wrapped droplet into a carrier fluid filled vessel,
    a thermocycler for amplifying the sample droplet; and
    at least one channel fluidly communicating the stage, the generator, the thermocycler and the port,
    wherein the droplet generator and the dispensing port are located lower than the at least one sample acquisition stage.

13. The system of claim 12 comprising a priming pump.

14. The system of claim 12 comprising an immiscible fluid removal pump.

15. A system for generating sample droplets comprising
    a variable height dispensing port;
    at least one sample acquisition stage located at a higher level than the dispensing port; and
    a droplet generator in fluid communication with the variable height dispensing port and the at least one sample acquisition stage, and
    a vessel for collecting the sample droplet dispensed from the port, the vessel configured to contain a carrier fluid for receiving and protecting the sample droplet;
    wherein the dispensing port is positioned below the level of the sample acquisition stage to create a siphoning effect, and wherein the droplet generator comprises an immiscible fluid for producing a sample droplet wrapped in an immiscible fluid.

16. The system of claim 15 wherein the system comprises at least one robotic system.

17. The system of claim 15 wherein the droplet generator is configured to wrap a droplet in the immiscible fluid.

18. The system of claim 15 wherein the distance between the sample acquisition stage and the dispensing port vary.

* * * * *

UNITED STATES PATENT AND TRADEMARK OFFICE
CERTIFICATE OF CORRECTION

PATENT NO. : 8,968,659 B2
APPLICATION NO. : 12/683882
DATED : March 3, 2015
INVENTOR(S) : Mark Davies et al.

It is certified that error appears in the above-identified patent and that said Letters Patent is hereby corrected as shown below:

In The Claims

Column 10, line 28, claim 13. reads "claim 12 comprising" should read --claim 12, further comprising--

Column 10, line 29, claim 14. reads "claim 12 comprising" should read --claim 12, further comprising--

Column 10, line 31, claim 15. reads "droplets comprising" should read --droplets, the system comprising--

Column 10, line 46, claim 16. reads "claim 15 wherein" should read --claim 15, wherein--

Column 10, line 48, claim 17. reads "claim 15 wherein" should read --claim 15, wherein--

Column 10, line 50, claim 18. reads "claim 15 wherein" should read --claim 15, wherein--

Column 10, line 51, reads "port vary." should read --port varies.--

Signed and Sealed this
Twenty-eighth Day of June, 2016

Michelle K. Lee
*Director of the United States Patent and Trademark Office*